United States Patent [19]
Clerkin

[11] Patent Number: 5,533,382
[45] Date of Patent: Jul. 9, 1996

[54] ABRASION TESTER

[75] Inventor: Thomas Clerkin, Athens, Ala.

[73] Assignee: Wire Technologies, Inc., St. Louis, Mo.

[21] Appl. No.: 468,422

[22] Filed: Jun. 6, 1995

[51] Int. Cl.[6] ................................................. G01N 3/56
[52] U.S. Cl. ............................... 73/7; 324/663; 73/150 R
[58] Field of Search ..................... 73/7, 150 R; 324/671, 324/672, 679, 663

[56] References Cited

U.S. PATENT DOCUMENTS

| | | |
|---|---|---|
| 2,177,528 | 10/1939 | Kidd ......................................... 324/671 |
| 2,329,062 | 9/1943 | Leape . |
| 2,372,093 | 3/1945 | Leape et al. . |
| 2,373,115 | 4/1945 | Graves . |
| 2,582,223 | 1/1952 | Blackburn et al. . |
| 3,150,523 | 9/1964 | Papsis . |
| 3,208,271 | 9/1965 | Thompson . |
| 4,734,545 | 3/1988 | Susuki et al. . |
| 4,780,662 | 10/1988 | Bennett et al. ........................... 324/671 |

FOREIGN PATENT DOCUMENTS 6-34506  2/1994  Japan .
6-160262  6/1994  Japan .

OTHER PUBLICATIONS

Cable Abrasion Tester Model No. CAT-1, Glowe–Smith Industrial, Inc., date unknown.
Military Specification Tester; Abrasion, Electrical Cable, MIL–T–5438, Dec. 19, 1949.
Society of Automotive Engineers, released 1995, Committee Draft–Aug., 1994, pp. 13–15.

*Primary Examiner*—Robert Raevis
*Attorney, Agent, or Firm*—Barnes & Thornburg

[57] ABSTRACT

An abrasion tester using an abrasive non-conductive strip moved along the first surface of a non-conductive material to be tested at a point of abrasion to abrade the material to be tested. The dielectric strength of the material to be tested and the abrasive strip at the point of abrasion between a first and second electrode is measured. The abrading process is stopped when a predetermined dielectric strength is measured. Determination is then made of acceptable abrasion resistance of the material to be tested as a function of the initiation and termination of abrading.

19 Claims, 1 Drawing Sheet

U.S. Patent   Jul. 9, 1996   5,533,382
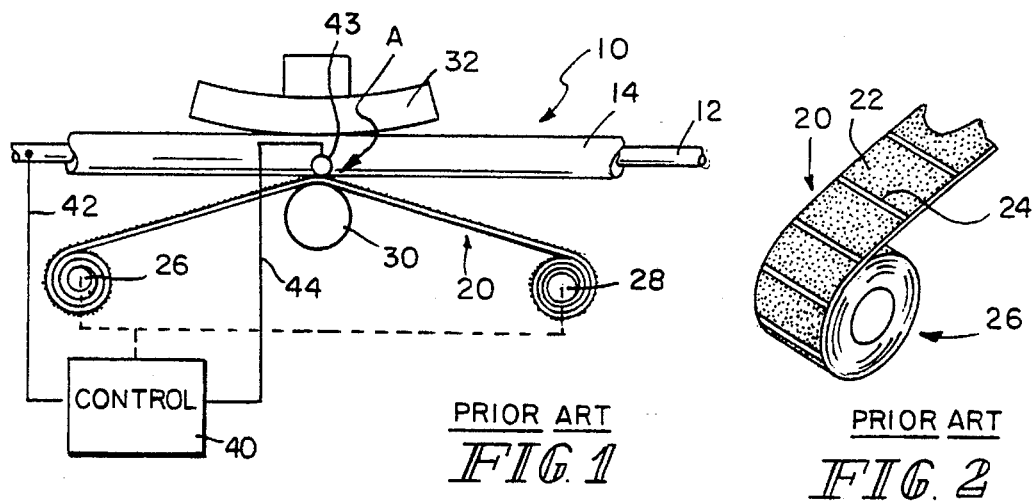
PRIOR ART
FIG. 1
PRIOR ART
FIG. 2
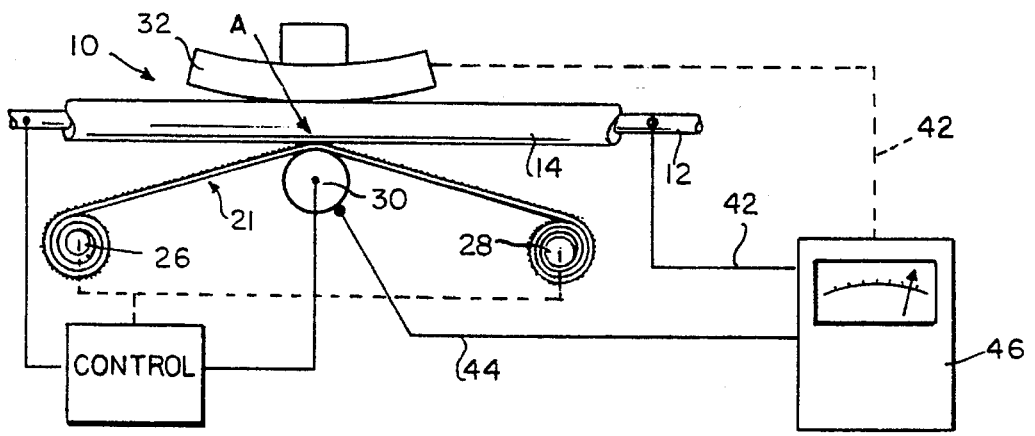
FIG. 3
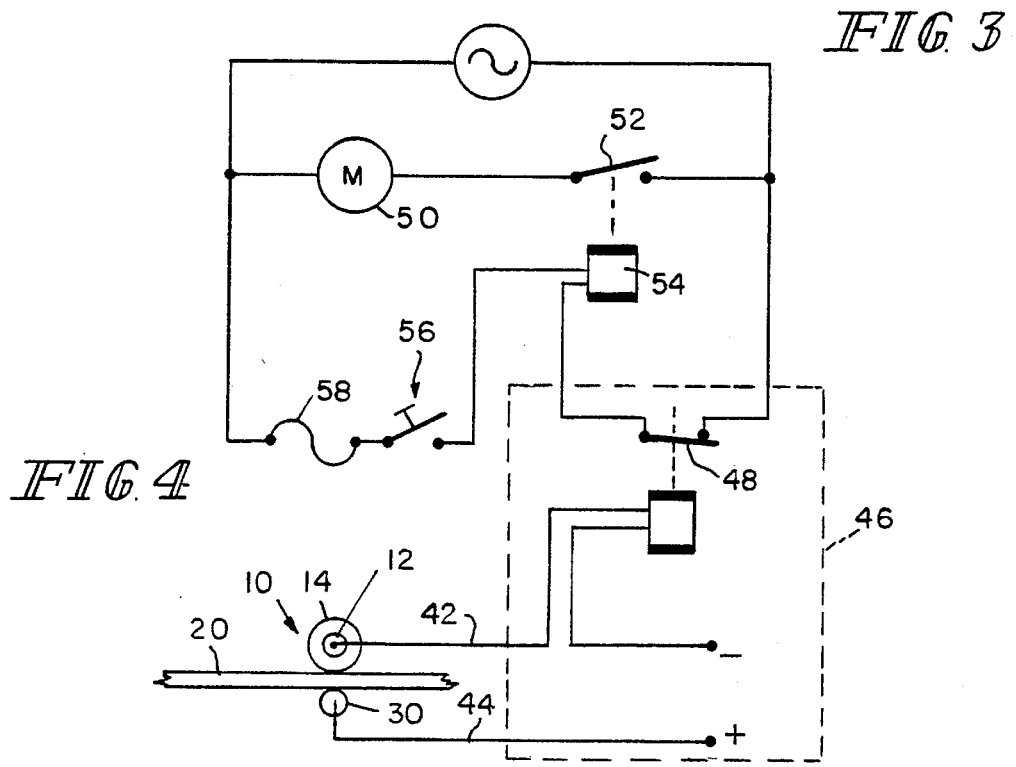
FIG. 4

ABRASION TESTER

SUMMARY AND BACKGROUND OF THE INVENTION

The present invention relates generally to an abrasion resistance testing and more specifically to abrasion resistance testing of non-conductive material.

Abrasion testers for testing the abrasion resistance of non-conductive materials, generally including insulative wires is well known. It generally includes securing the wire in a fixture and abrading at the point of abrasion until bare wire is exposed. A contact is made to the covered wire and the abrading tool is generally conductive. Thus, when the wire is exposed at the abrasion point, an electric circuit is completed. Acceptable abrasion resistance can then be determined as a function of the time period between the beginning of the abrasion process and when an electrical contact has been made to the wire at the point of abrasion. This testing process and equipment is described in military Specification MIL-T-5438 (19 Dec. 1949) and Society of Automotive Engineer SAE J1128 (1995).

The use of a piano wire as the abrading material and as a conductor of the sensor circuit is illustrated in U.S. Pat. No. 2,373,115. Moving the wire relative to a knife blade is illustrated in U.S. Pat. Nos. 2,329,062 and 2,372,093. Electrical contact is made by the blade to the interior wire. Applying weight to a blade until it pierces the installation is illustrated in U.S. Pat. No. 3,150,523.

A presently used system, for example, Model CAT-1 from Glowe-Smith Industrial, Inc. is illustrated in FIGS. 1 and 2. The insulative wire 10 includes internal conductors 12 and an insulative layer or insulator 14. An abrading or abrasive strip 20, as illustrated in FIG. 2, includes an abrasive surface 22 with spaced conductive segments 24 thereon. Strip 20 progresses from a supply roll 26 to a point of abrasion, point A, to a take up reel 28. The point of abrasion A is between a guide 30 for the abrasive strip 20 and a weight 32. A controller 40 is electrically connected to the wire conductor 12 by conductor 42 and to a sensing roller 43 on the top surface of abrasive strip 20 adjacent insulative wire 10 through conductor 44. The controller 40 controls a motor that drives the reels 26 and/or 28 and abrade the insulation 14 with the abrasive strip 20 until the wire conductor 12 is exposed at the abrasion point A. This exposure is determined by one of the conductive segments 24 coming into contact with the exposed wire conductors 12.

Since conductive segments 24 are spaced along the length of the abrasive strip, the point at which this contact is made is a function of the spacing of the conductor segments, and therefore is not extremely accurate. Also, the abrasive strip 20 with the conductive strips 24 is a specialty item and increases the cost of the tester. Another problem is that the conductor strips 24 are not of uniform quality. Their ability to make contact on the move would be a function of the spacing and force between the weight 32 and the guide 30 as well as the alignment of the roll. Thus, the results are very unreliable.

Thus, it is an object of the present invention to provide an abrasion tester which provides more accurate results.

Another object of the present invention is to provide an abrasive tester which is capable of using ordinary abrasive strips.

An even further object of the present invention is to provide an abrasive tester which does not require conductive contact with the wire conductor.

These and other objects are achieved by an abrasion tester using an abrasive non-conductive strip moved along the first surface of a non-conductive material to be tested at a point of abrasion to abrade the material to be tested. The dielectric strength of the material to be tested and the abrasive strip at the point of abrasion between a first and second electrode is measured. The abrading process is stopped when a predetermined dielectric strength is measured. Determination is then made of acceptable abrasion resistance of the material to be tested as a function of the initiation and termination of abrading.

The structure includes a fixture for retaining a non-conductive material to be tested. A driver drives the abrasive non-conductive strip along the material to be tested at the point of abrasion. The first and second electrodes are positioned so as to be separated by the material to be tested and the non-conductive abrasive strip. The dielectric strength measuring device is connected to the first and second electrodes. A controller starts the driver and stops the driver when the predetermined dielectric strength is measured. The strip material is a continuance strip fed from a feed spool to a take up spool past the point of abrasion. A conductive guide at the point of abrasion forms one of the electrodes. For the testing of insulative wire, the conductor of the insulative wires is second electrode. The predetermined dielectric strength is a value at which the material to be tested is worn through at the abrasion point. The length of tape used between the initiation and termination of the abrasion is used as an indication of the abrasion resistance. This length is measured or counted. The measuring device applies a voltage across the first and second electrode and measures the leakage current through the non-conductive material and strip therebetween as a measure of the dielectric strength.

Other objects, advantages and novel features of the present invention will become apparent from the following detailed description of the invention when considered in conjunction with the accompanying drawings.

BRIEF DESCRIPTION OF THE DRAWINGS

FIG. 1 is a diagrammatic view of an abrasion tester of the prior art.

FIG. 2 is a perspective view of an abrasive strip having conductive segments of the prior art.

FIG. 3 is a diagrammatic view of an abrasion tester incorporating the principles of the present invention.

FIG. 4 is a block diagram schematic of an abrasion tester incorporating the principles of the present invention.

DETAILED DESCRIPTION OF THE PREFERRED EMBODIMENTS

An abrasion tester, according to the principles of the present invention, is illustrated in FIG. 3. Those elements having the same purpose and structure as that of the prior art of FIG. 1 have the same reference number. By way of example, the non-conductive material to be tested is the insulative layer 14 on conductors 12 of wire 10. The wire conductor 12 and the insulator 14 are held in an appropriate fixture (not shown). The abrading material is illustrated as a continuous strip 21 being fed from the feed roller 26 to the take up roller 28 past a conductive guide 30 at the point of abrasion A.

The strip 21 is similar to the strip 20 of FIG. 1 having abrasive material 22 but excludes the conductive segments 24. The strip 21, for example, can be a paper substrate with particulate materials 22 thereon. Typically, this is sandpaper. Since this is not a special strip as in FIG. 1, it is substantially more inexpensive and various grits of sand paper can be used. Previously, 150 grit was the only grit that the special sandpaper with the conductive segments were provided. Since many values of grit sandpaper is available without conductive strips, this allows greater testing capability.

The non-conductive material to be tested is held between the weight 32 and the guide 30. Conductors 42 and 44 connect wire conductor 12 and the conductive guide 30 to a dielectric strength measuring device 46. As illustrated, it is a meter showing an electrical quantity representative of the dielectric strength of the material between the conductor 12 and the guide 30. The wire conductor 12 and the guide 30 form a pair of electrodes and the measuring device 36 applies a voltage across them. The dielectric therebetween is the insulative layer 14 and the abrasive strip 20. The dielectric strength value to be detected is the value at which the insulative layer 14 is worn through at the point of abrasion A. Thus, the dielectric would be the dielectric value of the abrasive strip 21. Substantially, no air gap should exist because of the weight 32 pressing the wire 10 and wire conductor 12 against guide or electrode 30. Such a measuring device 46 may be, for example, Model Series H300 AC/DC Hipot Testers and Megohmmeter from Hipotronics, Inc. Alternatively, any other form of capacitance, resistance or other electrical characteristic measuring device which provides non-contact indication that the insulation has abraded through at the abrading point can be used.

By using the dielectric strength measurements, no physical contact is made by the guide 30 and the wire conductors 12. This provides increased safety. It also removes any variation of measurement which is required by the mechanical contact between the two electrodes of the prior art. This substantially increases the accuracy of measurement of the time at which the insulative material 14 is worn through at the point of abrasion.

It should also be noted that the apparatus of FIG. 3 could be used to measure the abrasion resistance of any non-conductive material. The non-conductive material to be tested would be applied to a fixture and an appropriate electrode be placed such that the material to be tested is between the electrode and the guide 30. For example, the electrode may be applied to the face of the weight 30. A connection for such a testing is illustrated in phantom in FIG. 3 with the conductor 42. Thus, it can be seen in that of the abrasive tester can be used with other than insulated wires.

The measure of acceptable abrasion resistance is a function of the amount of time it takes to abrade the material. One way of measuring this time is to measure the length of the abrasive strip 21 between the initiation and termination of abrasion. This is the same measurement used in the prior art device of FIG. 1. With the structure of FIG. 3, the specific point at which abrasion has stopped, as determined by the measure device 46, is accurately determined. Alternatively, instead of measuring the length of abrasive strip 21 used, the time between initiation and termination of abrasion can also be used. Both of these concepts are well known in the prior art and are not described herein in detail. Reference is made to SE J1128 for example.

A controlled circuit for the system is illustrated in FIG. 4. The measuring device 46 includes a relay contact 48 in series with a relay 54, on-off switch 56 and a fuse 58 connected to a source of alternating current. Also connected in parallel with this circuit is a motor 50 and a relay contact 52 controlled by the coil or solenoid 54. The motor 50 is the drive motor for the reels 26 and 28 of the abrasive strip 21. The process is begun by closing on-off switch 56 activating solinoid 54 through closed relay contacts 48. This closes relay contacts 52 activating motor 50. The measuring device 46 applies a voltage across the insulative layer 14 of the device-under-test and the abrasive strip 20. When the value of leakage current exceeds that preset in the measuring device 46, contacts 48 are open breaking the circuit to relay 54. This opens relay contacts 52 and stops the motor 50.

The measuring device 46 can include a counter to either measure the time lapse between the motor being turned on and off or measuring the length of the tape dispensed. The measured quantity is then compared against a standard to determine acceptability of the abrasion resistance of the insulative material. The measuring device 46 has its own power source where connected to alternating current or a DC battery. As discussed previously, the measuring device 46 may be an HV300 series AC/DC Hipot Testers and Megohmmeters available from Hipotronics and thus a detailed schematic of the meter 46 is not provided herein.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. An abrasion tester for testing the abrasion resistance of a non conductive material comprising:

a fixture for retaining a non-conductive material to be tested;

an abrasive strip of non-conductive material and a driver to move the abrasive strip along a first surface of the material to be tested at a point of abrasion;

first and second electrodes separated by the material to be tested and the abrasive strip at the abrasion point;

a measuring device for measuring the dielectric strength of said non-conductive materials between the first and second electrodes; and a controller for stopping the driver when a predetermined dielectric strength is measured so as to determine abrasion resistance of the material to be tested as a function the initiation and termination of the driver.

2. An abrasion tester according to claim 1, wherein the abrasive strip is a continuous strip of non-conductive material and the driver includes a feed spool and a take up spool.

3. An abrasion tester according to claim 2, wherein the driver includes a guide for directing the abrasive strip to engage the material to be tested at the abrasion point.

4. An abrasion tester according to claim 1, wherein the driver includes a guide for directing the abrasive strip to engage the material to be tested at the abrasion point and the guide is the first electrode.

5. An abrasion tester according to claim 4, wherein the material to be tested is an insulative layer on a conductor and the conductor is the second electrode.

6. An abrasion tester according to claim 1, wherein the material to be tested is an insulative layer on a conductor and the conductor is one of the electrodes.

7. An abrasion tester according to claim 1, wherein the abrasive strip is a paper substrate with an abrasive particulate thereon.

8. An abrasion tester according to claim 1, wherein the predetermined dielectric strength is the value at which the material to be tested is worn through at the abrasion point.

9. An abrasion tester according to claim 1, including a strip measuring device for measuring the length of strip used between the initiation and termination of the driver as an indication of the abrasion resistance.

10. An abrasion tester according to claim 1, wherein the measuring device applies a voltage across the first and second electrodes and measures the leakage current through the non-conductive materials as a measure of the dielectric strength.

11. A method testing the abrasion resistance of a non conductive material comprising:

abrading a non-conductive material to be tested with an abrasive strip of non-conductive material at a point of abrasion;

measuring the dielectric strength of the material to be tested and the abrasive strip at the abrasion point between first and second electrodes;

stopping the abrading when a predetermined dielectric strength is measured; and determining abrasion resistance of the material to be tested as a function the initiation and termination of abrading.

12. A method according to claim 11, wherein said abrading includes moving a continuous, non-conductive abrasive strip from a feed spool past the abrasion point to a take up spool.

13. A method according to claim 12, including guiding the abrasive strip to engage the material to be tested at the abrasion point using one of the electrodes as a guide.

14. A method according to claim 11, including guiding the abrasive strip to engage the material to be tested at the abrasion point using the first electrode as a guide.

15. A method according to claim 14, wherein the material to be tested is an insulative layer on a conductor and the conductor is the second electrode.

16. A method according to claim 11, wherein the material to be tested is an insulative layer on a conductor and the conductor is one of the electrodes.

17. A method according to claim 11, wherein the predetermined dielectric strength is selected to be a value at which the material to be tested is worn through at the abrasion point.

18. A method according to claim 11, wherein determining abrasion resistance includes measuring the length of strip used between the initiation and termination of abrading.

19. A method according to claim 11 wherein measuring the dielectric strength includes applying a voltage across the first and second electrodes and measuring the leakage current through the non-conductive materials.

* * * * *